United States Patent [19]

Kulprathipanja et al.

[11] 4,367,364

[45] Jan. 4, 1983

[54] PROCESS FOR SEPARATING NORMAL PARAFFINS USING SILICALITE ADSORBENT

[75] Inventors: Santi Kulprathipanja, Hoffman Estates; Richard W. Neuzil, Downers Grove, both of Ill.

[73] Assignee: UOP Inc., Des Plaines, Ill.

[21] Appl. No.: 288,570

[22] Filed: Jul. 30, 1981

[51] Int. Cl.³ .................................................. C07C 7/12
[52] U.S. Cl. ............................... 585/826; 208/310 Z; 208/310 R; 585/827; 585/828
[58] Field of Search .................. 585/826, 827, 828; 208/310 R, 310 Z

[56] References Cited

U.S. PATENT DOCUMENTS

| | | | |
|---|---|---|---|
| 2,957,927 | 10/1960 | Broughton et al. | 260/676 |
| 3,150,079 | 9/1964 | Berlin | 585/827X |
| 3,239,455 | 3/1966 | Lickus et al. | 208/212 |
| 3,405,057 | 10/1968 | Neuzil | 585/826X |
| 4,000,059 | 12/1976 | Wanless | 208/310 |
| 4,006,197 | 2/1977 | Bieser | 585/826 |
| 4,061,724 | 12/1977 | Grose et al. | 423/335 |
| 4,309,281 | 1/1982 | Dessau | 208/310 Z |
| 4,329,280 | 5/1982 | Cleary et al. | 260/97.6 |

FOREIGN PATENT DOCUMENTS 1009974  11/1965  United Kingdom ............ 208/310 Z Primary Examiner—Delbert E. Gantz
Assistant Examiner—Asokkumar Pal
Attorney, Agent, or Firm—James R. Hoatson, Jr.; Louis A. Morris; William H. Page, II

[57] ABSTRACT

A process for separating a normal paraffin from a mixture of the same with another structural class of hydrocarbon selected from the cyclic hydrocarbons having greater than six carbons per molecule and the branched chain hydrocarbons. The process comprises contacting the mixture at adsorption conditions with an adsorbent comprising silicalite. The normal paraffin is selectively adsorbed and will preferably be recovered from the adsorbent by desorption with a desorbent material.

11 Claims, No Drawings

PROCESS FOR SEPARATING NORMAL PARAFFINS USING SILICALITE ADSORBENT

BACKGROUND OF THE INVENTION

The field of art to which this invention pertains is hydrocarbon separation. Specifically, this invention relates to a process which utilizes a crystalline silica composition and a desorbent to separate normal paraffins from a feed mixture of normal paraffins with certain other structural classes of hydrocarbons.

DESCRIPTION OF THE PRIOR ART

There is an abundance of prior art in the separation field, especially art relating to countercurrent fixed bed type operations, which deal with the separation of normal paraffins from other classes of hydrocarbons using a solid adsorbent. Examples of such art are U.S. Pat. Nos. 2,957,927 to Broughton et al; 3,239,455 to Lickus et al; 3,405,057 to Neuzil et al; 4,000,059 to Wanless; and 4,006,197 to Bieser. The most common adsorbent used throughout the prior art processes for the above separations are the crystalline aluminosilicates, the best known of which are the zeolites. The crystalline aluminosilicates function as "molecular sieves", that is, they contain pores having cross-sectional diameters which will accept certain molecules in a mixture of molecules of specific size and shape, i.e. normal paraffins; while rejecting others, i.e. branched chain and cyclic, thereby separating the accepted molecules from the mixture.

A new crystalline silica molecular sieve type adsorbent material known as "silicalite" has recently been invented. Silicalite is disclosed and claimed in U.S. Pat. No. 4,061,724 to Grose et al. The separation process utilizing silicalite contemplated by Grose et al comprises, in general terms, the separation of an organic compound from an aqueous solution. The organic molecules separated from their organic solutions in the separations exemplified in Grose et al are n-butanol, methyl cellosolve, methanol and phenol.

The present invention relates to a process for separating a normal paraffin from a mixture of the same with other structural classes of hydrocarbons using silicalite rather than the adsorbents known to the art for that separation. It has been discovered that silicalite is particularly suitable for such process.

SUMMARY OF THE INVENTION

In brief summary the invention is, in one embodiment, a process for separating a normal paraffin from a mixture of the same with another structural class of hydrocarbon selected from the cyclic hydrocarbons having greater than six carbon atoms per molecule and the branched chain hydrocarbons. The process comprises contacting the mixture at adsorption conditions with an adsorbent comprising silicalite to effect the selective adsorption of the normal aliphatic hydrocarbon by the adsorbent.

In another embodiment the present invention is a process for separating a normal paraffin from a mixture of the same with another structural class of hydrocarbon selected from the cyclic hydrocarbons having greater than six carbon atoms per molecule and the branched chain hydrocarbons. The process employs an adsorbent comprising silicate. The process comprises the steps of: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed input stream at an upstream boundary of the zone and a raffinate output stream at a downstream boundary of the zone; (c) maintaining a purification zone immediately upstream from the adsorption zone, the purification zone defined by the adsorbent located between an extract output stream at an upstream boundary of the purification zone and the feed input stream at a downstream boundary of the purification zone; (d) maintaining a desorption zone immediately upstream from the purification zone, the desorption zone defined by the adsorbent located between a desorbent input stream at an upstream boundary of the zone and the extract output stream at a downstream boundary of the zone; (e) passing the feed mixture into the adsorption zone at adsorption conditions to effect the selective adsorption of the normal paraffin by the adsorbent in the adsorption zone and withdrawing a raffinate output stream from the adsorption zone; (f) passing a desorbent material into the desorption zone at desorption conditions to effect the displacement of the normal paraffin from the adsorbent in the desorption zone; (g) withdrawing an extract output stream comprising the normal paraffin and desorbent material from the desorption zone; (h) withdrawing a raffinate output stream comprising the branched chain and cyclic hydrocarbons from the desorption zone; and (i) periodically advancing through the column of adsorbent in a downstream direction with respect to fluid flow in the adsorption zone, the feed input stream, raffinate output stream, desorbent input stream, and extract output stream to effect the shifting of zones through the adsorbent and the production of extract output and raffinate output streams.

Other embodiments of the present invention encompass details about feed mixtures, adsorbents, desorbent materials and operating conditions all of which are hereinafter disclosed in the following discussion of each of the facets of the present invention.

DESCRIPTION OF THE INVENTION

In order to gain a better understanding of the process of this invention, the following definitions of terms that are used throughout this specification are given.

The term "feed stream" indicates a stream in the process through which feed material passes to the adsorbent. A feed material comprises one or more extract components and one or more raffinate components. An "extract component" is a compound or type of compound that is more selectively adsorbed by the adsorbent while a "raffinate component" is a compound or type of compound that is less selectively adsorbed. In this process normal paraffins from the feed stream are extract components while feed stream isoparaffins and cyclic hydrocarbons are raffinate components. Usually the term extract component as used herein refers to a more selectively adsorbed compound or type of compound which is to be the desired product, such as normal paraffins in this process. The term "desorbent material" shall mean generally a material capable of desorbing an extract component. The term "desorbent stream" or "desorbent input stream" indicates the stream through which desorbent material passes to the adsorbent. The term "raffinate output stream" means a stream through which most of the raffinate components are removed from the adsorbent. The composition of the raffinate stream can vary from about 100% desorbent material to essentially 100% raffinate components. The term "extract stream" or "extract output stream" shall mean a stream through which an extract material which has been desorbed by a desorbent material is removed from the adsorbent. The composition of the extract stream can also vary from about 100% desorbent material to essentially 100% extract components.

Although it is possible by the process of this invention to produce high purity (99+%) normal paraffins at high recoveries (90% or higher), it will be appreciated that an extract component is never completely adsorbed by the adsorbent, nor is a raffinate component completely non-adsorbed by the adsorbent. Therefore, small amounts of a raffinate component can appear in the extract stream and, likewise, small amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of the adsorbed normal paraffins to that of the non-adsorbed components will be lowest in the raffinate stream, next highest in the feed mixture, and the highest in the extract stream. Likewise, the ratio of the concentration of the non-adsorbed components to that of the adsorbed normal paraffins will be highest in the raffinate stream, next highest in the feed mixture, and the lowest in the extract stream.

The term "selective pore volume" of the adsorbent is defined as the volume of the adsorbent which selectively adsorbs extract components from the feed stock. The term "non-selective void volume" of the adsorbent is the volume of the adsorbent which does not selectively retain extract components from the feed stock. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent.

When adsorbent "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components.

The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed stocks which can be used in the process of this invention will be hydrocarbon fractions having a carbon number range of from about two carbon atoms per molecule up to about 30 carbon atoms per molecule. Typically, the carbon number range of the hydrocarbon fractions will be rather narrow, such as from about three to about ten carbon numbers. A $C_{10}$–$C_{15}$ kerosine fraction or a $C_{10}$–$C_{20}$ gas oil fraction is a typical feed stream. Feed streams will contain normal paraffins, isoparaffins and cyclohydrocarbons, including aromatics having greater than six carbon atoms per molecule, in varying concentrations but little or no olefins. Depending on the type of crude from which the hydrocarbon fraction is derived and the carbon number range of the fraction, the normal paraffin concentration will typically range from about 15 to about 60 vol.% of the feed and the aromatic concentration from about 10 to about 30 vol.% of the feed. There may be more unusual feed streams which have aromatic concentrations of only about 2 to about 4 vol.% of the feed stream. Since the feed aromatics other than benzene, like the isoparaffins, cannot enter the pores of adsorbent used in this process because their cross-sectional diameter is too great, almost all of the aromatics appear in the raffinate stream. The feed aromatics can include monocyclic aromatics such as alkylbenzenes; indanes or alkylindanes; and bicyclic aromatics including naphthalenes, biphenyls, or the acenaphthenes.

Desorbent materials used in various prior art adsorptive separation processes vary depending upon such factors as the type of operation employed. In the swing bed system in which the selectively adsorbed feed component is removed from the adsorbent by a purge stream, desorbent selection is not as critical and desorbent materials comprising gaseous hydrocabons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high, nor would the desorbent material be available for reuse in the process. It is therefore contemplated that any desorbent material used in this process will preferably have a substantially different average boiling point than that of the feed mixture to allow separation of at least a portion of desorbent material from feed components in the extract and raffinate streams by simple fractional distillation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid-phase operation of the process of this invention, it has been found that desorbent materials comprising paraffins having average boiling points substantially different from that of a feed mixture meet these requirements and are particularly effective.

The adsorbent to be used in the process of this invention comprises the silicalite of Grose et al as previously mentioned. Silicalite is a hydrophobic crystalline silica molecular sieve. Due to its aluminum free structure, silicalite does not show ion-exchange behavior, and is hydrophobic and organophilic. Silicalite thus comprises a molecular sieve but not a zeolite. Silicalite is uniquely suitable for the separation process of this invention for the presumed reason that its pores are of a size and shape (about 6 angstrom units in diameter) that enable the silicalite to function as a molecular sieve, i.e. accept the molecules of normal paraffins into its channels or internal structure, while rejecting the molecules of hydrocarbons of other structural classes. A more detailed discussion of silicalite may be found in the article "Silicalite, A New Hydrophobic Crystalline Silica Molecular Sieve"; Nature, Vol. 271, Feb. 9, 1978, incorporated herein by reference.

The adsorbent may be employed in the form of a dense compact fixed bed which is alternatively contacted with the feed mixture and desorbent materials. In the simplest embodiment of the invention the adsorbent is employed in the form of a single static bed in which case the process is only semi-continuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used. The particles of silicalite adsorbent will preferably have a particle size range of about 16-60 mesh (Standard U.S. Mesh).

Countercurrent moving bed or simulated moving bed countercurrent flow systems have a much greater separation efficiency than fixed adsorbent bed systems and are therefore preferred. In the moving bed or simulated moving bed processes the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such flow system are described in U.S. Pat. No. 2,985,589 incorporated herein by reference. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of the process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feedstock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of the zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order tha the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of adsorbent that some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to ffect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 40° C. to about 250° C. and a pressure sufficient to maintain liquid-phase. Desorption conditions will include the same range of temperatures and pressures as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

Commercially available adsorbents heretofore used in the separation of the present invention have some entrance diameters less than 6 angstroms, examples of which are chabazite, Type A (both sodium and calcium forms), faujasite, mordenite, etc. A serious problem with these adsorbents is the low exchange rate for displacement of feed straight chain hydrocarbons with desorbent molecules and thus the long and inefficient cycle times required to effect desorption. The discovery leading to the present invention is that silicalite, which has some entrance diameters of 6 angstroms, does not exhibit such low exchange rate.

The following examples are presented to further illustrate the method of this invention but it is not intended to limit the invention to the operating conditions nor the materials disclosed therein.

EXAMPLE I

Commercially available clay bindered (about 20% by weight) 5A type Ca exchanged molecular sieves containing 2 wt.% water (pore entrance diameters of 5 angstroms) were obtained. A portion of these were evaluated for normal paraffin exchange in a dynamic test apparatus in the following manner. A first mixture of 16% n-tetradecane in isooctane was introduced into one end of a fixed bed thereby contacting a 40 cc bed of these fresh molecular sieves at 300 psig, 232° C. and 3 liquid hourly space velocity (LHSV). When the molecular sieve cavities were full of n-tetradecane as evidenced by a GLC analysis of the effluent from the other end of the fixed bed, a desorbent second mixture containing 16% chemically pure n-decane in chemically pure isooctane was introduced into one end of a fixed bed at the above conditions to effect the displacement of n-tetradecane within the sieve cavities by n-decane. This was continued until the effluent contained no n-tetradecane by GLC analysis. The first mixture was thereupon reintroduced into said one end again until the effluent contained no n-decane. The steepness of the concentration gradient for the appearance of n-tetradecane in the effluent was observed and taken as a measure of the rate of sorption of n-tetradecane.

Likewise, the steepness of the concentration gradient from the appearance of n-decane in the effluent was observed and taken as a measure of the rate of sorption of n-decane. The volume of the first mixture required to change the effluent from 10% to 90% of $n-C_{14}$ can be taken as a measure of the rate of sorption of $n-C_{14}$. The volume of the second mixture required to change the effluent from 10% to 90% of $n-C_{10}$ can be taken as a measure of the rate of sorption of $n-C_{10}$. In either case, the higher the volume the slower the rate of sorption. The volume required for the 10% to 90% change is hereinafter referred to as the "breakthrough slope".

For the above commercial adsorbent the breakthrough slope of $n-C_{10}$ was 60.0 ml, while that of $n-C_{14}$ was 12.8 ml.

EXAMPLE II

The test as set forth in Example I was repeated except that the adsorbent comprises silicalite particles in accordance with the present invention. The breakthrough slope observed for $n-C_{10}$ was 19.3 ml and that for $n-C_{14}$ was 12.6 ml.

The above data illustrates that the use of silicalite enables a much more rapid rate of sorption of $n-C_{10}$ as compared to the use of the commercial 5A adsorbent. Silicalite thus does not show a preference for one normal paraffin over another as exhibited by the 5A adsorbent, i.e. the n-paraffins are adsorbed and desorbed as a class.

Furthermore, unlike the commercial adsorbent which requires a relatively high water content (2 wt%) to function, the silicalite adsorption system needs no water. Water contamination of the product is then eliminated by use of silicalite.

What is claimed is:

1. A process for separating a normal paraffin from a mixture of the same with another structural class of hydrocarbon selected from the cyclic hydrocarbons having greater than six carbon atoms per molecule and the branched chain hydrocarbons, which comprises contacting said mixture at adsorption conditions with an adsorbent consisting essentially of silicalite to effect the selective adsorption of said normal aliphatic hydrocarbon by said adsorbent.

2. The process of claim 1 wherein said normal paraffin is recovered by desorption with a desorbent material at desorption conditions.

3. The process of claim 2 wherein said normal paraffin is in the group having from two up to about thirty carbon atoms per molecule.

4. The process of claim 2 wherein said desorbent material comprises a normal paraffin having a boiling point at least about 5° C. different than the boiling point of the normal paraffin being separated.

5. The process of claim 1 wherein said adsorption conditions include a temperature within the range of from about 40° C. to about 250° C. and a pressure sufficient to maintain liquid phase.

6. The process of claim 2 wherein said desorption conditions include a temperature within the range of from about 40° C. to about 250° C. and a pressure sufficient to maintain liquid phase.

7. A process for separating a normal paraffin from a mixture of the same with another structural class of hydrocarbon selected from the cyclic hydrocarbons having greater than six carbon atoms per molecule and the branched chain hydrocarbons, which process employs an adsorbent consisting essentially of silicalite, which process comprises the steps of:
   (a) maintaining net fluid flow through a column of said adsorbent in a single direction, which column contains at least three zones having separate operational functions occurring therein and being serially interconnected with the terminal zones of said column connected to provide a continuous connection of said zones;
   (b) maintaining an adsorption zone in said column, said zone defined by the adsorbent located between a feed input stream at an upstream boundary of said zone and a raffinate output stream at a downstream boundary of said zone;
   (c) maintaining a purification zone immediately upstream from said adsorption zone, said purification zone defined by the adsorbent located between an extract output stream at an upstream boundary of said purification zone and said feed input stream at a downstream boundary of said purification zone;
   (d) maintaining a desorption zone immediately upstream from said purification zone, said desorption zone defined by the adsorbent located between a desorbent input stream at an upstream boundary of said zone and said extract output stream at a downstream boundary of said zone;
   (e) passing said feed mixture into said adsorption zone at adsorption conditions to effect the selective adsorption of said normal paraffin by said adsorbent in said adsorption zone and withdrawing a raffinate output stream from said adsorption zone;
   (f) passing a desorbent material into said desorption zone at desorption conditions to effect the displacement of said normal paraffin from the adsorbent in said desorption zone;
   (g) withdrawing an extract output stream comprising said normal paraffin and desorbent material from said desorption zone;
   (h) withdrawing a raffinate output stream comprising said branched chain and cyclic hydrocarbons from said desorption zone; and
   (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams.

8. The process of claim 7 wherein said normal paraffin is in the group having from two up to about thirty carbon atoms per molecule.

9. The process of claim 7 wherein said desorbent material comprises a normal paraffin having a boiling point at least about 5° C. different than the boiling point of the paraffin being separated.

10. The process of claim 7 wherein said adsorption and desorption conditions include a temperature within the range of from about 40° C. to about 250° C. and a pressure sufficient to maintain liquid phase.

11. The process of claim 7 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

* * * * *